United States Patent [19]

Ester, deceased et al.

[11] 4,036,890
[45] July 19, 1977

[54] PREPARATION OF ORGANIC HYDROPEROXIDES

[75] Inventors: Wilhelm Ester, deceased, late of Herne, Germany; Margarete Ester, heir, Herne, Germany; Brigitte Louis nee Ester, heir, Herne, Germany; Wolfgang Ester, heir, Herne, Germany; Wilhelm Heitmann, Herne, Germany

[73] Assignee: Veba-Chemie AG, Gelsenkirchen-Buer, Germany

[21] Appl. No.: 454,963

[22] Filed: May 11, 1965

[30] Foreign Application Priority Data

May 13, 1964 Germany .................................. 35154

[51] Int. Cl.$^2$ ................. C07C 179/02; C07C 179/04
[52] U.S. Cl. ................................................. 260/610 B
[58] Field of Search ................................... 260/610 B

[56] References Cited

U.S. PATENT DOCUMENTS

| | | | |
|---|---|---|---|
| 2,632,772 | 3/1943 | Armstrong | 260/610 |
| 2,715,646 | 8/1955 | Hawkins | 260/610 |
| 3,559,661 | 7/1966 | Esters | 260/610 |

*Primary Examiner*—James O. Thomas, Jr.
*Assistant Examiner*—W. B. Lone
*Attorney, Agent, or Firm*—Burgess, Dinklage & Sprung

[57] ABSTRACT

Improvement in the known process for producing organic cyclic hydroperoxides, which process includes oxidizing a compound of the formula

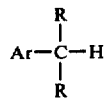

wherein Ar is an aromatic or saturated cycloaliphatic radical and each R is an aliphatic hydrocarbon radical or a hydrogenated bicyclic terpene hydrocarbon hydroperoxide with an oxygen-containing gas at a temperature of about 80°–150° C under a pressure of about atmospheric up to about 10 atms., wherein the product, when produced by this process, has an improved activity on the catalysis of olefin polymerization if the oxidation reaction is halted at the point where the produced hydroperoxide has a concentration in the reaction mass of about one to less than 5%.

9 Claims, No Drawings

PREPARATION OF ORGANIC HYDROPEROXIDES

This invention relates to the production of organic hydroperoxides and more particularly relates to the production of cyclic hydroperoxides and particularly those derived from aromatic or hydroaromatic (cycloaliphatic) hydrocarbon base materials substituted with at least one alkyl group containing a hydrogen on the aliphatic carbon atom adjacent the ring constituent.

Cyclic hydroperoxides are well-known materials. They are used to great advantage in olefin polymerization as initiators or catalysts. It is known to produce a cyclohydroperoxide by oxidizing a substituted aromatic or cycloaliphatic compound using oxygen-containing gases. In the past it has been the practice in the production of cyclo-hydroperoxides to add alkaline-active materials, such as alkali hydroxides, for instance, sodium or potassium hydroxide, or to effect the oxidation without the addition of alkali but with the maintenance of the pH of the oxidation reaction mixture at a value of no less than 3.

As with most industrially important organic syntheses, it has been the strong desire to modify and improve the processes for producing cyclo-hydroperoxides in order to increase the yield obtained and thus to make the process more efficient. Some of the improvements in this regard have been mentioned above. Another such improvement which is known is to conduct the oxidation reaction so that a concentration of 5 to 10% by weight of hydroperoxide is produced. The thus produced hydroperoxide solution is then washed with an alkaline solution and with water to produce by further oxidation further quantities of hydroperoxide and to thereby increase the percent conversion of reaction to hydroperoxide and therewith the concentration of hydroperoxide in the reaction mixture. This technique has been used with success with terpene hydrocarbons, such as, for example, p-methane with a view toward decreasing by-product formation. It has not been found to be convenient for improving the production of aromatic hydroperoxides because the product purity obtained in accordance with this procedure does not significantly change from the aromatic hydroperoxide product purity obtained by utilizing relatively short reaction times with or without alkali additions.

The prior art then can be seen to be directed toward production of high purity organic hydroperoxides in high reaction yields and conversions and, in accordance with some of the techniques, as mentioned above, achieve reaction mixture concentrations as high as 75% hydroperoxide.

Since the primary utility for the products of this invention reside in their use as olefin polymerization initiators and catalysts, the true measure of the value of any such given product is in its ability to catalyze or to initiate such polymerization.

It is then the principal object of this invention to produce organic cyclic hydroperoxides which show greater activity as olefin polymerization initiators or catalysts than the products heretofore available.

Another object of this invention is to produce organic cyclic hydroperoxides which are purer than those previously produced.

A further object of this invention is to provide a new method of producing organic cyclic hydroperoxides suitable for use as improved olefin polymerization catalysts of initiators.

Other and additional objects will be apparent from a consideration of the following specification.

In accordance with and fulfilling the objects thereof, this invention comprises, in one of its aspects, the oxidation of compounds of the formula

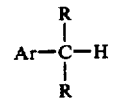

wherein Ar is an aromatic or cycloaliphatic moiety, as for instance phenyl, cyclohexyl, cycloheptyl, and their alkylated derivatives with 1 to 5 hydrocarbon atoms in the alkylated group, and the like, and each R is an aliphatic hydrocarbon radical such as methyl, ethyl, propyl, and homologs thereof, of hydrogen or hydrogenated bicyclic terpene hydrocarbon hydroperoxides i.e. pinan, carane and the like, with an oxygencontaining gas such as air, air-enriched with oxygen, oxygen or mixtures of oxygen and inert gases, at a temperature of about 80° to 150° C. under atmospheric or slightly elevated pressures up to about 10 atmospheres. The hydroperoxidecontaining reaction mixture thus obtained is intimately mixed with aqueous alcoholic solutions or suspensions of alkaline-active materials; particularly, it is desirable to utilize such solutions or suspensions in dilute concentrations, e.g., about 1 to 50 wt. % of alkaline-active material. Suitable alkaline-active materials include alkali metal or alkaline earth metal carbonates and hydroxides. This class of materials is well-known and may be exemplified by sodium, potassium, lithium, magnesium, barium, calcium, and like hydroxides or carbonates. It is advisable in connection with the mixing to employ a centrifugal pump in which the hydroperoxide solution is mixed with the alkaline-active material under turbulent flow conditions. Reaction times of under 5 seconds, and preferably between 0.2 and 0.8 seconds, are satisfactory. Mixing is also possible by means of other suitable and conventional stirring devices, such as blade stirrers, but under such circumstances longer mixing times, as for example up to and more than 15 minutes, should be used.

It has been most surprisingly found that cyclic hydroperoxides produced according to the above process possess unusually great activity in initiating or catalyzing olefin polymerizations if the above described reaction is permitted to proceed only so far as to produce a reaction mixture containing about 1 to 5% by weight of cyclic hydroperoxide and preferably only 3 to 4% by weight cyclic hydroperoxide.

While it is not known exactly why cyclic hydroperoxides produced in accordance with the process above described should possess, and do possess, such greatly improved catalytic activity, it is believed that by stopping the reaction at this very low conversion point the formation of certain as yet unidentified impurities is suppressed.

The cyclic hydroperoxide produced according to this invention can be separated from the reaction mixture and formed into more concentrated solutions if desired. The reaction mixture can also be subjected to an alkaline wash and, if necessary, a water-washing treatment following oxidation. The reaction mixture, i.e. oxidate, can also be introduced directly following the oxidation into a concentration stage where it can be, for example, brought to higher concentration using a film evaporator of a conventional construction provided with a distillation column as, for example, described in German Pat. No. 1,082,254.

More particularly, the hydroperoxide produced according to the invention may be concentrated and separated from the reaction mixture by extraction and decantation, wherein it is separated into an aqueous and organic phase. The upper layer contains the hydroperoxide dissolved in hydrocarbon in the form of an emulsion which cannot be worked up directly. Treatment of this product with a suitable washing agent such as with water or a mono or polyvalent alcohol - for instance, methanol or ethylene glycol or glycerol - results in an extremely rapid and clear separation of the layers. The treatment is carried out in a second separator and a very pure hydroperoxide solution separating out as the upper layer. The lower layer which still contains considerable amounts of hydroperoxide and hydrocarbon is introduced into the first alkaline washing step so that losses are completely avoided. Here, the addition is advantageously effected before the first separator as this produces a dilution of the added alkali right in the apparatus, and the washing agent is again used in the dilution process.

The oxidate can also be led directly to the concentration stage without any intermediate treatment.

This process can be carried out continuously or batchwise as desired. It is preferred to operate continuously wherein the oxidation vessel is continuously charged with the same amount of starting hydrocarbon as is drawn off as hydroperoxide solution. The mixture then goes to the first separator, the upper layer being continuously drawn off and washed with a washing agent in the subsequently arranged pump while the lower layer from the first separator remains partly in circulation. A portion of the flow is constantly withdrawn and replaced by addition of further alkaline solution. The aqueous or alkaline solutions drawn off can be purified, for instance, by filtration and ion exchange and re-introduced into the washing process. The lower layer from the second separator is then returned to the first separator. The hydroperoxide solution thus obtained can be worked up by vacuum distillation or, alternatively, by using film evaporators.

The process is especially suited for the preparation of hydroperoxides which may be used as radical catalysts, in particular, cumene-hydroperoxide, cymene-hydroperoxide diisopropylbenzenemonohydroperoxide, p-menthane-hydroperoxide, pinane-hydroperoxide, and other commercial hydroperoxides of this type.

The following examples are given by way of illustration of the instant invention but are in no wise limitative thereof. In the Examples parts and percentages are by weight unless expressly stated to be on another basis:

EXAMPLE 1 p-Menthane was pumped continuously into an oxidation reactor and a corresponding amount of oxidate solution was drawn off in such an amount that the hydroperoxide concentration in the reactor remained at a constant level under operating conditions. This p-menthane was oxidized at a reactor temperature of 120° C., a pressure of about 3.8 atm., an oxygen content in the effluent gas of 1.8% and a p-menthane hydroperoxide content in the reactor of 3.0%. The oxidation product which was withdrawn from the reactor was washed with a dilute sodium carbonate solution and with water and then concentrated by distillation in a film evaporator to a content of p-menthane hydroperoxide in the sump effluent of 79.5%.

EXAMPLE 2

The process of Example 1 was repeated except that the reaction was permitted to proceed to a p-menthane hydroperoxide concentration in the reactor of 4.5%. The p-menthane hydroperoxide in the evaporator sump effluent was 80.9%.

EXAMPLE 3

Employing the process of Example 1, the reaction was permitted to proceed to a p-menthane hydroperoxide concentration in the reactor of 7.0%, the p-menthane hydroperoxide in the evaporator sump effluent amounted to 73.1%.

EXAMPLE 4

The procedure set out in Example 1 was again conducted. In this case the reaction was continued to a p-menthane hydroperoxide concentration in the reactor of 10.0% and a p-menthane hydroperoxide concentration in the evaporator sump effluent of 64.6%.

The p-menthane hydroperoxide concentrations obtained in Example 1–4 were diluted by addition thereto of p-menthane in an amount sufficient to produce a hydroperoxide concentration of 54%. The activity of these peroxide examples in the emulsion polymerization of butadiene-styrene at +5° was determined according to the procedure described in Polymer Process, p. 156, et seq., C. E. Schildknecht. The polymerization mixture which was used was that described in the Kautschuk-Handbuch, Vol. 1 Stuttgart 1959, p. 357, for SBR 1500. The amount of polymerized material obtained in 14 hours polymerization time using p-menthane hydroperoxide which had been oxidized in the reactor to 4.5% peroxide was taken as resulting from a hydroperoxide having an activity of 100. All other activities as shown in the table are in relation to this value.

Table I

| Peroxide level in the reactor | Activity |
|---|---|
| 3.0% | 103.3 |
| 4.5% | 100.0 |
| 7.0% | 93.4 |
| 10.0% | 79.7 |

The comparison clearly shows the superiority of the concentrates which had been oxidized to less than 5% in accordance with the invention.

EXAMPLE 5

A mixture of p- and m- diisopropylbenzene was oxidized continuously at 120° C. employing the process of Example 1. The hydroperoxide level permitted in the reactor was 2.8%. Purification and concentration was carried out as described in Example 1. The hydroperoxide product was evaluated in the polymerization reaction corresponding to that set out above.

EXAMPLE 6

Example 5 was repeated with the exception that the reaction was permitted to proceed to a diisopropylbenzene-hydroperoxide concentration in the reactor of 3.9%.

EXAMPLE 7

Example 5 was repeated with the exception that the reaction was permitted to proceed to a diisopropylbenzene-hydroperoxide concentration in the reactor of 7.6%.

EXAMPLE 8

Employing the process of example 5, the reaction was continued until the diisopropylbenzene-hydroperoxide concentration amounted to 21.1%.

EXAMPLE 9

The procedure of Example 5 was repeated. In this instance, the oxidation was continued until a hydroperoxide concentration of 30.1% was reached.

The activities of the hydroperoxides produced in accordance with Examples 5-9 were determined. The hydroperoxide products were diluted to equal concentrations prior to use. The results of the comparison are set out in Table II which follows:

Table II

| Peroxide level in the reactor | Activity |
|---|---|
| 2.8 % | 116.8 |
| 3.9 % | 113.4 |
| 7.6 % | 104.7 |
| 21.1 % | 94.5 |
| 30.1 % | 81.7 |

A consideration of Table II establishes that the oxidates which were oxidized to hydroperoxide contents of under 5% had a considerably higher activity than those where oxidation amounted to more than 5% and that these products produced the highest volume-time polymer yields.

Concentrates (1) obtained in Example 5 (oxidation to a peroxide concentration in the reactor of 2.8%) was mixed with synthetically prepared p-isopropyl-acetophenone (2) and with p-isopropylphenylene-dimethylcarbonol (3). These latter products represent typical by-products of the oxidation reaction. The activity of various mixtures thus produced is represented in Table III which follows:

Table III

| | | | Activity |
|---|---|---|---|
| 50% (1) | | 50 diisopropylbenzene | 116.8 |
| 50% (1) | + 10% (2) | 40 diisopropylbenzene | 111.4 |
| 50% (1) | + 10% (3) | 40 diisopropylbenzene | 110.5 |
| 50% (1) | + 10% (2) + 10% (3) | 30 diisopropylbenzene | 107.6 |

The activity values which are set out above and which are only slightly decreased as compared with the results as set out in Table II indicate clearly that the main oxidation by-products cannot be chiefly responsible for the marked decrease in activity when oxidation is carried out to a higher peroxide concentration. It is to be thought that those substances which are not as yet identified exert a specific detrimental influence on the course of the polymerization are produced as an adjunct in the production of hydroperoxide at higher reactor concentrations. Formation of these detrimental substances is avoided in accordance with the invention by production of low hydroperoxide concentrations in the reactor during oxidation.

We claim:

1. In the production of organic cyclic hydroperoxides which comprises oxidizing a compound selected from the group consisting of compounds of the formula:

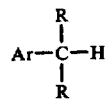

wherein Ar is a member selected from the group consisting of phenyl, cyclohexyl and cycloheptyl, which can be substituted by $C_{1-5}$ alkyl and each R is an aliphatic hydrocarbon radical, and compounds of the group consisting of carane, pinane, p-menthane and camphane with an oxygen-containing gas at a temperature of about 80° to 150° C and a pressure of about atmospheric up to about 10 atmospheres; the improvement which comprises halting said oxidation when the concentration of produced hydroperoxide reaches about 1 to less than 5% by weight in the reaction mixture, and recovering said cyclic hydroperoxide.

2. The process claimed in claim 1, wherein oxidation is halted at a hydroperoxide concentration of about 3 to 4% by weight.

3. The process claimed in claim 1, wherein the compound which is oxidized is p-menthane.

4. The process claimed in claim 1, wherein the compound which is oxidized is diisopropyl-benzene.

5. The process claimed in claim 1, wherein the compound which is oxidized is cumene.

6. The process claimed in claim 1, wherein the compound which is oxidized is pinane.

7. The process claimed in claim 1, wherein the compound which is oxidized is cymene.

8. Process according to claim 1, which comprises concentrating said oxidation product following said washing.

9. In the production of organic cyclic hydroperoxide which comprises oxidizing a compound selected from the group consisting of compounds of the formula:

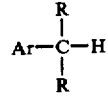

wherein Ar is a member selected from the group consisting of phenyl, cyclohexyl, cycloheptyl, which can be substituted by $C_{1-5}$ alkyl, and each R is an aliphatic hydrocarbon radical, and compounds of the group consisting of carane, pinane, p-menthane and camphane with an oxygen-containing gas at a temperature of about 80°–150° C and a pressure of about atmospheric up to about 10 atmospheres, washing the oxidation product with an alkaline agent dispersed in a member selected from the group consisting of water and alcohol, and recovering said cyclohydroperoxide from said washed oxidation product; the improvement which comprises halting said oxidation when the concentration of produced hydroperoxide reaches about one to less than 5% by weight in the reaction mixture.

* * * * *